United States Patent
Datta et al.

(10) Patent No.: US 9,963,660 B2
(45) Date of Patent: May 8, 2018

(54) METHOD OF CLEANING WITH ENHANCED BACTERIOSTATIC ACTION USING A COMPOSITION OF ALCOHOL AND LACTATE ESTERS

(71) Applicants: Rathin Datta, Chicago, IL (US); George D. Laubach, Elgin, IL (US)

(72) Inventors: Rathin Datta, Chicago, IL (US); George D. Laubach, Elgin, IL (US)

(73) Assignee: Vertec Biosolvent, Inc., Downers Grove, IL (US)

( * ) Notice: Subject to any disclaimer, the term of this patent is extended or adjusted under 35 U.S.C. 154(b) by 0 days. days.

(21) Appl. No.: 15/099,879

(22) Filed: Apr. 15, 2016

(65) Prior Publication Data

US 2016/0304814 A1   Oct. 20, 2016

Related U.S. Application Data

(60) Provisional application No. 62/178,792, filed on Apr. 20, 2015.

(51) Int. Cl.
| | | |
|---|---|---|
| *C11D 3/20* | (2006.01) | |
| *C11D 1/66* | (2006.01) | |
| *C11D 1/62* | (2006.01) | |
| *C11D 3/48* | (2006.01) | |
| *A01N 31/02* | (2006.01) | |
| *C11D 3/43* | (2006.01) | |
| *C11D 7/26* | (2006.01) | |
| *C11D 7/50* | (2006.01) | |

(52) U.S. Cl.
CPC ............... *C11D 3/48* (2013.01); *A01N 31/02* (2013.01); *C11D 3/201* (2013.01); *C11D 3/2093* (2013.01); *C11D 3/43* (2013.01); *C11D 7/261* (2013.01); *C11D 7/266* (2013.01); *C11D 7/5022* (2013.01)

(58) Field of Classification Search
CPC ........ C11D 3/2086; C11D 3/2003; C11D 3/48
See application file for complete search history.

(56) References Cited

U.S. PATENT DOCUMENTS

| | | | | |
|---|---|---|---|---|
| 4,222,905 A * | 9/1980 | Cockrell, Jr. | ............ | C11D 1/38 510/295 |
| 4,295,217 A * | 10/1981 | Fennel, Jr. | .............. | H04J 3/177 370/201 |
| 5,454,970 A * | 10/1995 | Flaningam | ........... | C11D 7/5095 134/38 |
| 8,574,609 B2 * | 11/2013 | Lopes | .................... | A01N 37/36 424/405 |
| 2003/0125225 A1 * | 7/2003 | Xu | ........................ | B08B 7/0021 510/175 |
| 2009/0173917 A1 * | 7/2009 | Allen | ..................... | A61K 31/22 252/364 |
| 2010/0233146 A1 * | 9/2010 | McDaniel | .............. | A01N 63/02 424/94.2 |
| 2012/0040880 A1 * | 2/2012 | Rieth | ....................... | A61K 8/39 510/138 |
| 2014/0147395 A1 * | 5/2014 | Rieth | ..................... | C11B 9/008 424/49 |
| 2016/0304814 A1 * | 10/2016 | Datta | .................... | A01N 31/02 |

* cited by examiner

*Primary Examiner* — Nicole M Buie-Hatcher
*Assistant Examiner* — M. Reza Asdjodi
(74) *Attorney, Agent, or Firm* — Husch Blackwell LLP

(57) ABSTRACT

A mixture of ethanol and lactate esters have enhanced cleaning properties for food and biological processing applications and this mixture retains bacteriostatic properties during the cleaning process as well as in the used cleaning solutions after rinsing and dilution with water.

7 Claims, No Drawings

METHOD OF CLEANING WITH ENHANCED BACTERIOSTATIC ACTION USING A COMPOSITION OF ALCOHOL AND LACTATE ESTERS

CROSS-REFERENCE TO RELATED APPLICATION

This application claims priority from application Ser. No. 62/178,792 that was filed on Apr. 20, 2015, whose disclosures are incorporated herein by reference.

BACKGROUND ART

Cleaning and sanitization of vessels, process equipment, pipes, valves, lines, membranes and many other components that are used in food processing, biological processing and other operations are necessary and widely practiced. Typically, aqueous solutions often containing surfactants are used for the cleaning operations. For sanitization a variety of biocidal or bacteriostatic chemicals and reagents are used. The surfactants and chemicals that are used for such processes are too numerous to elaborate further. Dilution and rinsing with water before the equipment and process is ready for further operation is another important and necessary feature.

Solvents are sometimes used for such cleaning methods particularly for cleaning of difficult contaminants such as fats and denatured proteins, which can form coating layers. Alcohols are also sometimes used in combination with surfactants, polyols or other reagents.

Alcohols are known to have bacteriostatic properties and often ion exchange resins, ultrafiltration membranes and other bio-sensitive processing agents are kept in aqueous alcohol solutions for bacteriostatic preservations [*Handbook of Disinfectants and Antiseptics*, J. M. Ascenzi ed., Marcel Dekker, Inc, New York (1996); "Use of Benzyl Alcohol as a shipping and Storage Solution for Chromatography Media", *GE Healthcare and Life Sciences*, Application Note 28-9899-01AB, General Electric Company bulletin, (2012); Barker et al., *Appl Environ Microb*, 67(4):1594-2000 (2001); and Oh et al., *Int J Food Microbiol*, 20:239-246 (1993)]. Organic acids such as formic, acetic, lactic are also known to have bacteriostatic properties ["Use of Benzyl Alcohol as a shipping and Storage Solution for Chromatography Media", *GE Healthcare and Life Sciences*, Application Note 28-9899-01AB, General Electric Company bulletin, (2012); Barker et al., *Appl Environ Microb*, 67(4):1594-2000 (2001); and Oh et al., *Int J Food Microbiol*, 20:239-246 (1993)], but they have limited cleaning properties for fats, proteins and other biological contaminants.

A combination of alcohols, organic acids and other reagents can be used for cleaning and sanitization, but such combination compositions usually suffer from at least two major limitations: —1) the cleaning properties are primarily determined by the alcohol, and 2) dilution with water during and after cleaning, reduces both the solvent activity and the bacteriostatic activity.

BRIEF SUMMARY OF THE INVENTION

Ethanol and ethyl lactate are both solvents and separately have some use in cleaning of contaminated surfaces, particularly of food processing equipment and vessels. A mixture of ethanol and ethyl lactate has enhanced cleaning properties compared to either of them independently. A good effective composition of the mixture contains about 80% to about 50% ethanol by weight (w/w) and the remainder is primarily ethyl lactate.

The solvent mixture is or can be used with water dilution prior to or during the cleaning process or as a neat solvent followed by rinsing with water. Typical dilution amounts are about 1 volume to about 1.5 volumes (1:1.5) to about 1 volume to about 2.5 volumes (1:2.5) or about 30 to about 70 percent. In this three-part composition of ethyl alcohol (component A), ethyl lactate (component B) and water (component C) the weight percentages of the components are: Component A at about 80% to about 35%, Component B at about 50 to about 14% and Component C at about 0% to about 30%, wherein the sum of Components A, B and C total to 100%.

In either case, the added water enables the hydrolysis of the lactate ester, thereby producing ethanol and lactic acid, and slowly lowering the pH value. The resulting production of added ethanol, lactic acid and the pH drop increases the bacteriostatic activity of the cleaning mixture during the cleaning process itself.

Furthermore, this bacteriostatic activity is maintained in the used cleaning solution after rinsing and further dilution with water.

These actions are unique and are enabled by the composition and properties of the solvent mixture and its use in the cleaning process.

A contemplated cleaning composition can also be used in conjunction with a surfactant, component D. When so used, component D is present at about 1 to about 10 w/w % of the total composition, with the percentages of Components A, B and C being reduced in proportion to the amount of component D added.

DETAILED DESCRIPTION OF THE INVENTION

Cleaning and sanitization of vessels, process equipment, pipes, valves, lines, membranes and many other components that are used in food processing, biological processing and other operations are necessary and widely practiced. Typically, aqueous solutions that often contain surfactants are used for the cleaning operations. For sanitization, a variety of biocidal or bacteriostatic chemicals and reagents is used. The surfactants and chemicals that are used for such processes are too numerous to elaborate further, but are well known to workers in the cleaning and sanitation arts. Dilution and rinsing with water before the equipment and process is ready for further operation is another important and necessary feature.

Oftentimes, difficult contaminants such as fats and denatured proteins, which can form coating layers, are not readily cleaned by aqueous surfactant solutions. The presence of these contaminants also can cause microbial growth that can lead to unacceptable odors and sometimes growth of pathogenic organisms. Some examples of such pathogens are *Listeria* and *Salmonella* species.

The present invention contemplates a mixture of ethanol and ethyl lactate that has enhanced cleaning properties compared to either of them independently. Such a composition contains about 80% to about 50% ethanol and the remainder is primarily ethyl lactate.

The solvent mixture is or can be used with water dilution prior to or during the cleaning process, or as a neat solvent followed by rinsing with water. Typical dilution amounts are about 1 volume to about 1.5 volumes (1:1.5) to about 1 volume to about 2.5 volumes (1:2.5) or about 30 to about 70 percent. In this three-part composition of ethyl alcohol (component A), ethyl lactate (component B) and water (component C) the weight percentages of the components are: Component A at about 80% to about 35%, Component B at about 50 to about 15% and Component C at about 0% to about 30%, wherein the sum of Components A, B and C total to 100%.

This solvent and water mixture undergoes slow hydrolysis and the effectiveness of the solvent mix during the cleaning period is maintained over a long period of time. Further dilution with water during cleaning and rinsing e.g., to about 1 to about 10 volumes (1:10) to about 1 to about 20 volumes (1:20) enables continued hydrolysis of the lactate ester producing ethanol and lactic acid and lowering the pH value. All of which increases the bacteriostatic activity of the cleaning mixture during the cleaning and rinsing process steps. Furthermore, this bacteriostatic activity is maintained in the used cleaning solution after rinsing and further dilution with water.

These cleansing and bacteriostatic activities are unique and are enabled by the composition and properties of the solvent mixture alone and on dilution of the solvent mixture with water during its use in the cleaning process. It is emphasized that when ethanol and ethyl lactate are separately diluted at about 1:10 to about 1:20, neither resulting diluted composition retains its bacteriostatic effect as well as does a contemplated ethanol plus ethyl lactate composition.

A contemplated cleaning composition can also contain a non-ionic, cationic or anionic surfactant. A surfactant (component D) is admixed into the mixture in an amount to provide a concentration of component D at about 1 to 10 w/w % of the total composition, with the percentages of Components A, B and C being reduced in proportion to the amount of component D added.

Exemplary non-ionic surfactants include linear long chain, e.g., $C_{10}$-$C_{18}$, alcohol ethoxylate ethers sold under the name Surfonic® L12-3 made by Huntsman Chemical Company which is a typical 3 mole ethoxylate of mixed linear primary 10 to 12 carbon number alcohols. Similar long chain alcohol ethoxylates of individual alcohols such as lauryl (C12), myristyl (C14), palmityl (C16) and stearyl (C18) alcohols are commercially available named for the common alcohol minus the suffix "yl" and with a new suffix "eth" followed by a hyphen and numeral that indicates the average number of ethylene oxide (PEG) groups per molecule such as laureth-3 and steareth-10.

PEG-3 to PEG-11 cocamide, a polyethylene glycol amide of cocoa fatty acids containing an average of the numeral following "PEG" ethylene oxide groups. Ethoxylated nonylphenols are also useful and commercially available under the generic name of nonoxynol followed by a hyphen and a number that indicates the number of ethylene oxide groups bonded to the phenolic hydroxyl group such as nonoxynol-2 and nonoxynol-12. Similar ethoxylated octylphenols are commercially available under the generic name octoxynol followed by a hyphen and a numeral indicating the average number of oxyethylene groups per molecule such as octoxynol-5 and octoxynol-8.

Useful anionic surfactants are preferably sulfonates, as carboxylates can build up on surfaces after several uses and sulfate esters can exhibit stability problems. Illustrative sulfonate surfactants include the long chain alkylbenzene sulfonates such as isopropylamine dodecylbenzene sulfonate made by Stepan Company and sold under the name NINATE® 411 was also readily soluble in excess of 20% w/w in two solvent compositions of 80/20. Other alkylbenzene sulfonate surfactants include sodium cetylbenzenesulfonate and disodium lauryl phenyl ether disulfonate.

Still further sulfonates include the long chain alkane sulfonates such as the C13-C17 alkane and C14-C18 alkane sulfonates and the ethoxylated long chain alcohol sulfonates such as those sold under the name sodium C12-C15 pareth-3 sulfonate and the sodium C12-C15 pareth-7 sulfonate that have an average of 3 oxyethylene and 7 oxyethylene groups per C12-C15 alcohol, respectively.

Cationic surfactants can be generally viewed as the reaction product of a long chain alkyl halide compound with a trisubstituted amine to produce a long chain alkyl trisubstituted ammonium halide compound. Such compounds are illustrated by of mono-long chain di-methyl or -diethyl benzyl ammonium salts, that are also useful herein. Thus, for example, mixed $C_{12}$-$C_{18}$ alkyl benzyl dimethyl or diethyl quaternary ammonium salts are also highly soluble in excess of 20% in the solvent mixtures. Further, the material sold commercially as benzalkonium chloride is a chloride salt of a mixture of $C_{10}$-$C_{18}$ alkyl dimethyl benzyl ammonium compounds. Another useful cationic surfactant is sold as cetrimonium bromide, can be viewed as the reaction product of trimethylamine and cetyl bromide.

Still further examples of non-ionic, anionic and cationic surfactants will be apparent to those skilled in the detergent/surfactant arts and need not be recited here.

Properties of solvents are often evaluated and expressed in measured and calculated values of solubility parameters and a few other physical constants. A property table for the solvents ethanol, ethyl lactate and water and the solvent mixtures of ethanol and ethyl lactate are provided in Table 1.

TABLE 1*

| Solvent or Blend | Viscosity Cp @ 25 C. | Surface Tension (mN/m) | SPo | SPd | SPp | SPh |
|---|---|---|---|---|---|---|
| Ethanol (EtOH) | 0.43 | 22.2 | 13.0 | 7.7 | 4.3 | 9.5 |
| Ethyl lactate (EtLa) | 2.41 | 28.6 | 10.6 | 7.8 | 3.7 | 6.1 |
| Water | 0.9 | 72.0 | 23.4 | 7.6 | 7.8 | 20.7 |
| Blend 1 EtOH:EtLa 80:20 | 0.83 | 23.5 | 12.4 | 7.7 | 4.2 | 8.8 |
| Blend 2 EtOH:EtLa 50:50 | 1.4 | 25.4 | 11.7 | 7.7 | 4.0 | 7.8 |

*Solubility parameters: SPo = Hildebrand; SPd = Disperse; SPp = Polar; and SPh = hydrogen bonding parameter.

As mentioned before, lactic acid and other organic acids such as acetic acid have no significant solvent properties.

The property table above shows some differences between the solvents and the blends particularly in the hydrogen bonding (SPh) parameter. It is not apparent however, by the property evaluation alone that one would be able to conclude that the solvent blend would have an enhanced cleaning action.

Ethanol is known to have a strong denaturing action on proteins and denaturation can be detrimental because in many contaminated surfaces the fats, proteins and other biomolecules are juxtaposed in undefined configurations such as micelles, vesicles and other molecular as well as macromolecular structures that can be denatured and made more difficult to remove. Ethyl lactate has some unique attributes because it can interact with both hydrophilic and hydrophobic molecules because of its hydroxyl and carboxyl ester group, and can thereby often serve as a bridging solvent. Nevertheless, it is not predictable that the solvent blend would provide a better cleaning action than the individual solvents.

The following examples provide support for this invention.

Example 1: Cleaning Solvating Action Differences in Laboratory Tests

Peanut butter is a complex mixture of fats, carbohydrates and proteins that are emulsified in processing equipment under controlled conditions. Because of its composition that contains all the major food groups and because the product is made by controlled food processing methods, peanut butter was chosen for an initial cleaning examination.

Commercially available Skippy® peanut butter made by Best Foods Company was used. Commercially available metal screen mesh (size 20 mesh) was cut into small (25 mm×75 mm), equal sized strips that were dipped into heated (about 50° C.) peanut butter and then drip dried in air. Excess was removed, which resulted in the strips being coated with a thin and consistent layer of the peanut butter (PB).

For the solvent evaluation studies, beakers containing the solvents were placed in a water bath (40° C.), the solvents were stirred at the same speed, the pre-weighed strips were dipped into the solvent at the same depth for a time period of 20 minutes. The strips were then dried under forced air at room temperature and their weights were measured periodically. After 90 minutes of drying the test results were evaluated to determine the comparative differences between the effects of the solvent compositions.

Commercial grade of ethanol is typically denatured by small quantities of additives. Ethyl acetate is an approved denaturant for ethanol and it is non-toxic for food and biological related applications. In all of the examples for this invention the ethanol used was denatured by about 5% (w/w) ethyl acetate.

The first set of studies was conducted with neat solvents; i.e., no additional water was added to the test solvents. The results are summarized in Table 2a.

TABLE 2a

| Solvent Tested | Weight of initial PB (g) | Weight of final PB (g) | Weight loss (g) | Percent Removal |
|---|---|---|---|---|
| Ethanol | 2.0122 | 1.602 | 0.41 | 20.4 |
| Ethyl Lactate | 1.787 | 1.656 | 0.131 | 7.3 |
| 80% ethanol + 20% ethyl lactate | 1.783 | 1.405 | 0.378 | 21.2 |
| 50% ethanol + 50% ethyl lactate | 1.734 | 1.387 | 0.347 | 20.0 |

The second set of tests was conducted with neat solvents plus 30 wt % water added to the test solvents. The results are of these studies summarized in Table 2b.

TABLE 2b*

| Solvent Tested | Weight of initial PB (g) | Weight of final PB (g) | Weight loss (g) | Percent Removal* |
|---|---|---|---|---|
| 70% Ethanol + 30% $H_2O$ | 2.657 | 2.815 | −0.158 | −5.9 |
| 70% Ethyl Lactate + 30% $H_2O$ | 2.474 | 2.7283 | −0.254 | −10.3 |
| 56% ethanol + 14% ethyl lactate + 30% $H_2O$ | 2.034 | 2.061 | −0.027 | −1.3 |
| 35% ethanol + 35% ethyl lactate + 30% $H_2O$ | 1.332 | 0.90 | 0.432 | 32.4 |

*Negative values show retention rather that removal.

Some unusual and unexpected results are shown in these studies. With the neat solvents, the removal efficiency by the mixed solvents are better than that of the ethyl lactate and are in the same range as with ethanol alone. However, when water was added, the pure solvents did not show any removal, but rather exhibited an actual increase in the mass, most likely due to retention of water inside the peanut butter layer. With the mixed solvents, this water retention was very low or negligible and actual removal took place.

In the actual practice of cleaning processes, removal of water is very difficult and expensive, and water is often added as a diluent and rinse. Hence the use of these mixed solvents clearly showed an advantage.

Example 2: Performance in Larger Scale Use

A large-scale test with actual vessels and equipment was conducted. These were heavily contaminated during food preparation and processing of meat and vegetables, and could not be satisfactorily cleaned by the normal cleaning agents containing aqueous surfactants and other chemicals. Furthermore, they had objectionable odors caused by biological contamination.

A mixture of ethanol (80% w/w) and ethyl lactate (20% w/w) was blended on line (metered flow) with water to provide an about one-half dilution (about equal amounts of the solvent blend and water) and used with spray and agitation to clean these vessels and equipment. The online mixing enabled the solvent blend to go directly into the cleaning action and then undergo hydrolysis over time.

The results were very positive. The cleaning was very satisfactory and met the desirable standards. Moreover the objectionable odors were eliminated.

Example 3: Surfactant Solubility in Mixtures

In addition to the solvent effects, surfactants are also useful and can provide additional cleaning activity. Several types of surfactants were found to be highly soluble in the solvent mixtures.

The non-ionic surfactants of linear alcohol ethoxylate ethers were readily soluble. For example Surfonic® L12-3 made by Huntsman Chemical company which is a typical 3 mole ethoxylate of linear primary 10 to 12 carbon number alcohol, was readily soluble in excess of 20% w/w in two solvent compositions of 80/20 ethanol/ethyl lactate and 50/50 ethanol/ethyl lactate.

The anionic surfactants of isopropylamine dodecylbenzene sulfonate made by Stepan Company under the name NINATE® 411 was also readily soluble in excess of 20% w/w in two solvent compositions of 80/20 ethanol/ethyl lactate and 50/50 ethanol/ethyl lactate.

Cationic surfactants, which are generally mixtures of quaternary ammonium salts of alkyl ($C_{12}$-$C_{18}$) dimethyl benzene or diethyl benzene are also highly soluble in excess of 20% in the solvent mixtures.

Example 4: Ester Hydrolysis of Mixture

Two separate compositions of ethanol, ethyl lactate and water were tested over a period of time to determine the rate of the ester hydrolysis as would be typical during a cleaning period of several hours.

Composition 1 was a mixture of 56% ethanol, 14% ethyl lactate and 30% water (all wt. %). The molar % ratios were: ethanol 40.5%, ethyl lactate 4.1% and water 55.5%. An aliquot of the mixture was removed, its pH value measured and titrated with 0.1 N sodium hydroxide solution to determine the titrable acidity and calculate the hydrolysis of the ethyl lactate.

Composition 2 was a mixture of 35% ethanol, 35% ethyl lactate and 30% water (all wt. %). The molar % ratios were: ethanol 27.9%, ethyl lactate 10.9% and water 61.2%. An aliquot of the mixture was removed, its pH measured and titrated with 0.1 N sodium hydroxide solution to determine the titrable acidity and calculate the hydrolysis of the ethyl lactate.

The data are shown in Table 3.

TABLE 3

| Time (hours) | pH (initial) | pH (end point) | mMol of alkali added | % ethyl lactate hydrolyzed |
|---|---|---|---|---|
| Composition 1 | | | | |
| 0.5 | 5.84 | 7.5 | 0.065 | 0.11 |
| 1 | 5.8 | 7.6 | 0.07 | 0.12 |
| 2 | 5.8 | 7.6 | 0.07 | 0.12 |
| 6 | 5.8 | 7.2 | 0.07 | 0.12 |
| 96 | 5.7 | 7.5 | 0.09 | 0.15 |
| Composition 2 | | | | |
| 0.5 | 4.91 | 6.02 | 0.21 | 0.142 |
| 1 | 4.84 | 6.09 | 0.23 | 0.155 |
| 2 | 4.84 | 6.09 | 0.27 | 0.182 |
| 6 | 4.88 | 6.02 | 0.27 | 0.182 |
| 96 | 4.75 | 7.0 | 0.71 | 0.48 |

These data clearly show that during a typical cleaning time of several hours with moderate dilution with water (30% by weight) the rate of ester hydrolysis is very slow and the integrity of the solvent mix components during the 4-day cleaning period is maintained.

Example 5: Bacteriostatic Activity and Tests

Methods to determine minimum inhibitory concentrations (MIC) of biocides or bacteriostatic agents that work in processing liquids to inhibit biological growth have been developed and optimized (U.S. Pat. No. 5,206,151). Typically, such MIC determinations involve (a) obtaining a known volume aliquot of the contaminated aqueous system and (b) adding thereto a known amount of an oxidation reduction indicator dye, which indicator dye is capable of reacting with dehydrogenase enzymes produced by the microbiological organisms, and also (c) adding sufficient nutrients capable of accelerating microbiological organism activity, thereby forming a reaction product between reducing enzymes and the oxidation-reduction indicator dye. Multiple aliquots of the indicator dye treated and nutrient treated, aqueous system are transferred to a microtitration plate containing multiple sample wells (d), each well containing but one of the multiple aliquots. (e) Serially diluted amounts of at least one antimicrobial agent is added to at least one column (or row) of these sample wells on the titration plate, provided that a single column (or row) is treated with only one antimicrobial agent, that at least one column (or row) is left untreated to thereby form a treated titration plate. The treated titration plate is incubated at a temperature essentially equivalent to the temperature of the contaminated aqueous system from which the aliquot was originally taken and maintained for a period of time sufficient to develop the change in the indicator dye color by the reaction of the indicator dye with reducing enzymes produced by nutrient acceleration of microbiological metabolism (f). The first change in color in dye relative to the untreated column is noted (g) to determine the minimum inhibitor concentration of antimicrobial agent that inhibits growth of microbiological organism contained in the contaminated aqueous system.

Such a method is optimized under the Trademark of MiniTox™ and tests are routinely practiced and results provided by microbiological testing laboratories such as: The MicroStar Lab Ltd located at 130 Erick Street in Crystal Lake, Ill. 60014.

A cleaning solution of VERTECBIO® ELSOL™ IPAR which is 80% ethanol and 20% ethyl lactate was diluted five-fold with water as would typically occur during a cleaning followed by rinsing process. This solution was kept as is at room temperature and hydrolysis of the ester continued. This solution was serially diluted with broth and media components for the MiniTox tests in microtiter plates. Two bacterial cultures *Salmonella Choleraesuis* ATCC 10708 and *Listeria Monocytogenis* ATCC 19115 were used for the studies. Bacteria of the *Salmonella* species are known pathogens that contaminate meat and vegetable types of food and *Listeria* species are known to contaminate milk and related foods.

The results clearly show:

1) At a 5% concentration (i.e. 20× dilution) the VERTECBIO® ELSOL™ IPAR solution controlled the growth of *Salmonella Choleraesuis*, and a 2.5% concentration (i.e. 40× dilution) slowed the growth rate. Ethanol or ethyl lactate alone diluted to the same extent does not exhibit bacteriostatic activity.

2) At a 10% concentration (i.e. 10× dilution) the VERTECBIO® ELSOL™ IPAR solution controlled the growth of *Listeria Monocytogenis* and 5% concentration (i.e. 20× dilution) slowed the growth rate. Ethanol or ethyl lactate alone diluted to the same extent does not exhibit bacteriostatic activity.

Each of the patents, patent applications and articles cited herein is incorporated by reference. The articles "a" and "an" are used herein to refer to one or to more than one (i.e., to at least one) of the grammatical object of the article. By way of example, "an element" means one element or more than one element.

The foregoing description and the examples are intended as illustrative and are not to be taken as limiting. Still other variations within the spirit and scope of this invention are possible and will readily present themselves to those skilled in the art.

The invention claimed is:

1. A method for cleaning surfaces and equipment contaminated by fats, proteins and other biomaterials comprising applying to a surface to be cleaned a water-dilutable cleaning composition that is a mixture of $C_2$-$C_3$ aliphatic alcohol (component A), ethyl lactate (component B), a surfactant (component D) and water (component C) where the concentration (w/w %) of component A is about 80% to about 35%, the concentration of component B is about 50 to about 14%, component C is about 0% to about 30%, and component D is zero to about 10%, wherein the sum of Components A, B, C and D total to 100%, said mixture being a more effective cleaner than the individual components themselves and wherein the mixture retains its bacteriostatic activity during and after the cleaning operation.

2. The method according to claim 1, wherein the concentration of component D is about 1 to about 10 w/w % of the total composition.

3. The method according to claim 1, wherein said surfactant is present and is a nonionic, cationic or a sulfonate anionic surfactant.

4. The method according to claim 3, wherein said nonionic surfactant is present and is a long chain alcohol ethoxylate.

5. The method according to claim 3, wherein said anionic surfactant is present and is a long chain alkylbenzene sulfonate.

6. The method according to claim 3, wherein said cationic surfactant is present and is a long chain alkyl trisubstituted ammonium halide compound.

7. The method according to claim 1, wherein said $C_2$-$C_3$ aliphatic alcohol is ethanol.

\* \* \* \* \*